US008628485B2

(12) United States Patent
Wilson et al.

(10) Patent No.: US 8,628,485 B2
(45) Date of Patent: Jan. 14, 2014

(54) GAIT ANALYSIS SYSTEM AND METHODS

(75) Inventors: Richard R. Wilson, Arden Hills, MN (US); Douglas R. Oudekerk, Saint Paul, MN (US); Douglas P. Wilson, Madison, WI (US); Karla M. Fogel, Evanston, IL (US); Rebecca Neth Townsend, Bellevue, WA (US)

(73) Assignees: Covenant Ministries of Benevolence Inc., Chicago, IL (US); Richard R. Wilson, Arden Hills, MN (US); Douglas R. Oudekerk, Saint Paul, MN (US); Douglas P. Wilson, Madison, WI (US)

( * ) Notice: Subject to any disclaimer, the term of this patent is extended or adjusted under 35 U.S.C. 154(b) by 448 days.

(21) Appl. No.: 12/851,614

(22) Filed: Aug. 6, 2010

(65) Prior Publication Data
US 2012/0035509 A1 Feb. 9, 2012

(51) Int. Cl.
*A61B 5/103* (2006.01)
(52) U.S. Cl.
USPC .............................. 600/592; 600/595; 73/172
(58) Field of Classification Search
USPC .................................... 600/592, 595; 73/172
See application file for complete search history.

(56) References Cited

U.S. PATENT DOCUMENTS

| 5,952,585 | A | 9/1999 | Trantzas et al. |
|---|---|---|---|
| 6,231,527 | B1 | 5/2001 | Sol |
| 6,360,597 | B1 * | 3/2002 | Hubbard, Jr. ............... 73/172 |
| 6,807,869 | B2 | 10/2004 | Farringdon et al. |
| 6,836,744 | B1 | 12/2004 | Asphahani et al. |
| 7,191,644 | B2 | 3/2007 | Haselhurst et al. |
| 7,526,954 | B2 | 5/2009 | Haselhurst et al. |
| 7,587,937 | B2 | 9/2009 | Haselhurst et al. |
| 2003/0009308 | A1 | 1/2003 | Kirtley |
| 2003/0097878 | A1 | 5/2003 | Farringdon et al. |
| 2004/0143452 | A1 | 7/2004 | Pattillo et al. |
| 2005/0184878 | A1 | 8/2005 | Grold et al. |
| 2007/0021689 | A1 | 1/2007 | Stergiou et al. |
| 2008/0041169 | A1 | 2/2008 | Walczyk et al. |
| 2008/0053253 | A1 | 3/2008 | Moore et al. |
| 2008/0146968 | A1 | 6/2008 | Hanawaka et al. |
| 2008/0167580 | A1 | 7/2008 | Avni et al. |

(Continued)

FOREIGN PATENT DOCUMENTS

TW 200838475 10/2008

OTHER PUBLICATIONS

Akhlaghi, F. et al., "In-shoe biaxial shear force measurement: the Kent shear system," *Medical & Biological Engineering & Computing*, vol. 34, pp. 315-317 (Jul. 1996).

*Primary Examiner* — Max Hindenburg
*Assistant Examiner* — Renee Danega
(74) *Attorney, Agent, or Firm* — Merchant & Gould P.C.

(57) ABSTRACT

Systems and methods for analyzing the gait of an individual are disclosed. The disclosed systems and methods can be configured to acquire data from a first array and a second array of sensors that are configured to be placed in a left and/or right shoe, respectively. The acquired data can be collected or separated into at least two separate gait phases for each array, compared to a baseline condition for each gait phase and categorized into one of at least two uniformity categories for each gait phase. Examples of collected and/or calculated data include pressure values, shear stress values and torque values. The analysis can be focused on both feet of a person, or focused on one foot. A graphical output showing at least one entire gait cycle based on the uniformity categories can then be generated.

19 Claims, 16 Drawing Sheets

(56) References Cited

U.S. PATENT DOCUMENTS

| | | |
|---|---|---|
| 2008/0287832 A1* | 11/2008 | Collins et al. .............. 600/587 |
| 2008/0292179 A1 | 11/2008 | Busch |
| 2009/0124938 A1 | 5/2009 | Brunner |
| 2009/0163834 A1* | 6/2009 | Wilssens ................. 600/592 |
| 2009/0198155 A1 | 8/2009 | Bonnet |
| 2009/0293319 A1 | 12/2009 | Avni |
| 2010/0035727 A1 | 2/2010 | Brunner |

* cited by examiner

FIG. 12

Identification Information for Gait Data Recording

| Subject | | Date and Time | |
|---|---|---|---|
| Name:<br>Birth date:<br>Gender:<br>Height:<br>Weight: | | Start date:<br>Start time:<br>Stop date:<br>Stop time:<br>Duration: | |

FIG. 13

Baseline Period Gait Data

| Parameter | Number | % |
|---|---|---|
| 2A. Left foot contacts (FCs): number with at least 1 recorded gait phase | | NA |
| • # and % of left FCs with 3 recorded gait phases | | |
| • # and % of left FCs with less than 3 recorded gait phases | | |
| • # and % of left FCs with more than 3 recorded gait phases* | | |
| • Left FC baseline total pressures (sum of all pressure values recorded) | Pressure | NA |
|     ○ Heel strike – mean | | NA |
|     ○ Heel strike – median | | NA |
|     ○ Mid stance – mean | | NA |
|     ○ Mid stance – median | | NA |
|     ○ Toe off – mean | | NA |
|     ○ Toe off – median | | NA |
| • Left FC baseline mean pressures (mean of all pressure values recorded) | Pressure | NA |
|     ○ Heel strike – mean | | NA |
|     ○ Heel strike – median | | NA |
|     ○ Mid stance – mean | | NA |
|     ○ Mid stance – median | | NA |
|     ○ Toe off – mean | | NA |
|     ○ Toe off – median | | NA |
| 2B. Right foot contacts (FCs): number with at least 1 recorded gait phase | | NA |
| • # and % of right FCs with 3 recorded gait phases | | |
| • # and % of right FCs with less than 3 recorded gait phases | | |
| • # and % of right FCs with more than 3 recorded gait phases* | | |
| • Right FC baseline total pressures (sum of all pressure values recorded) | Pressure | NA |
|     ○ Heel strike – mean | | NA |
|     ○ Heel strike – median | | NA |
|     ○ Mid stance – mean | | NA |
|     ○ Mid stance – median | | NA |
|     ○ Toe off – mean | | NA |
|     ○ Toe off – median | | NA |
| • Right FC baseline mean pressures (mean of all pressure values recorded) | Pressure | NA |
|     ○ Heel strike – mean | | NA |
|     ○ Heel strike – median | | NA |
|     ○ Mid stance – mean | | NA |
|     ○ Mid stance – median | | NA |
|     ○ Toe off – mean | | NA |

Note: * = at least one gait phase repeated during a single foot contact; % = percentage; # = number; FCs = foot contacts; NA = not applicable

FIG. 14

Evaluation Period Gait Data and Comparison with Baseline Period Gait Data

| Parameter | Number | % | Change in % from Baseline |
|---|---|---|---|
| 3A. Left foot contacts (FCs): number with at least 1 recorded gait phase<br>• # and % of left FCs with 3 recorded gait phases<br>• # and % of left FCs with less than 3 recorded gait phases<br>• # and % of left FCs with more than 3 recorded gait phases* | | NA | NA |
| • Left FC evaluation total pressures (sum of all pressure values recorded)<br>    ○ Heel strike – mean<br>    ○ Heel strike – median<br>    ○ Mid stance – mean<br>    ○ Mid stance – median<br>    ○ Toe off – mean<br>    ○ Toe off – median | Pressure | NA<br>NA<br>NA<br>NA<br>NA<br>NA<br>NA | NA |
| • Left FC evaluation mean pressures (mean of all pressure values recorded)<br>    ○ Heel strike – mean<br>    ○ Heel strike – median<br>    ○ Mid stance – mean<br>    ○ Mid stance – median<br>    ○ Toe off – mean<br>    ○ Toe off – median | Pressure | NA<br>NA<br>NA<br>NA<br>NA<br>NA<br>NA | |
| 3B. Right foot contacts (FCs): number with at least 1 recorded gait phase<br>• # and % of right FCs with 3 recorded gait phases<br>• # and % of right FCs with less than 3 recorded gait phases<br>• # and % of right FCs with more than 3 recorded gait phases* | | NA | NA |
| • Right FC evaluation total pressures (sum of all pressure values recorded)<br>    ○ Heel strike – mean | Pressure | NA<br>NA | |

FIG. 15

Evaluation Period Gait Data and Comparison with Baseline Period Gait Data Cont.

|  |  |
|---|---|
| ○ Heel strike – median | NA |
| ○ Mid stance – mean | NA |
| ○ Mid stance – median | NA |
| ○ Toe off – mean | NA |
| ○ Toe off – median | NA |
| • Right FC evaluation mean pressures (mean of all pressure values recorded) | Pressure NA |
| ○ Heel strike – mean | NA |
| ○ Heel strike – median | NA |
| ○ Mid stance – mean | NA |
| ○ Mid stance – median | NA |
| ○ Toe off – mean | NA |

3C. Comparison of pressures of left FCs with right FCs
- Heel strike – # of left FCs with mean pressure >25% above right FC
- Heel strike – # of left FCs with median pressure >25% above right FC
- Heel strike – # of right FCs with mean pressure >25% above left FC
- Heel strike – # of right FCs with median pressure >25% above left FC
- Mid stance – # of left FCs with mean pressure >25% above right FC
- Mid stance – # of left FCs with median pressure >25% above right FC
- Mid stance – # of right FCs with mean pressure >25% above left FC
- Mid stance – # of right FCs with median pressure >25% above left FC
- Toe off – # of left FCs with mean pressure >25% above right FC
- Toe off – # of left FCs with median pressure >25% above right FC
- Toe off – # of right FCs with mean pressure >25% above left FC
- Toe off – # of right FCs with median pressure >25% above left FC

FIG. 16

Evaluation Period Gait Data and Comparison with Baseline Period Gait Data Cont.

---

3D. Identification of unexpected gait phase sequences
- Left foot
    - # and % of FCs with heel strike as last recorded phase in gait cycle
    - # and % of FCs with heel strike as only recorded phase in gait cycle
    - # and % of FCs with no heel strike recorded in gait cycle
- Right foot
    - # and % of FCs with heel strike as last recorded phase in gait cycle
    - # and % of FCs with heel strike as only recorded phase in gait cycle
    - # and % of FCs with no heel strike recorded in gait cycle

---

Note: * = at least one gait phase repeated during a single foot contact; % = percentage; # = number; FCs = foot contacts; NA = not applicable

ND METHODS

TECHNICAL FIELD

This application relates to a system and methods for collecting, calculating and outputting data useful in analyzing the gait of an individual.

BACKGROUND

Disorders of asymmetries and/or imbalances in gait have been associated with significant clinical morbidity, mortality, and healthcare cost and resource utilization. For example, loss of balance and falls can result in acute injuries, hospitalization, and deaths. Additionally, the progressive deterioration of the joints, either with associated pain or without pain, can cause balance/gait disorders. For example, injuries to the anterior cruciate ligament can lead to deterioration of the knee joint anatomy and function. Another example is the deterioration at the knee or hip joint anatomy and function secondary to rheumatoid arthritis and/or osteoarthritis, either before or after partial or total hip joint replacement surgery. Yet another cause of balance/gait disorders is unequal weight bearing between the lower extremities, resulting in chronic musculoskeletal pain, including back pain. As might be appreciated, numerous challenges exist in preventing, treating and rehabilitating balance and gait disorders.

Even though the causes for many balance and gait disorders are well understood, improvements in assessment tools for analyzing these disorders are desired. This is particularly the case where it is desired to assess gait and/or balance quantitatively during the totality of ambulation and activity over a prolonged period, for example, over the course of a full day.

SUMMARY

Systems and methods for analyzing the gait of an individual are disclosed. In one method, data are acquired from a first array and a second array of pressure sensors and/or shear stress sensors that are configured to be placed in a left and right shoe, respectively. By the use of the term "shoe" it is broadly intended to mean any foot appliance suitable for fitting sensors that will be on or near an individual's foot. By way of non-limiting examples, a shoe can be a walking shoe, a dress shoe, a running shoe, a sandal, a slipper, or a foot appliance designed for the specific purpose of assessing a person's gait. The acquired data are collected or separated into at least two separate gait phases for each array and then compared to a baseline condition for each gait phase. The pressure sensors in the array are then categorized into one of at least two pressure uniformity categories for each gait phase based on the results of the comparison of the acquired data to the baseline condition. A graphical output showing at least one entire gait cycle based on the pressure uniformity categories can then be generated. An additional graphical output showing shear stress and resultant torque values can be overlaid onto the graphical output showing the pressure uniformity categories. It should also be noted that the system can be used to evaluate a single foot of an individual, or can be used to evaluate both feet.

In another method, data are acquired onto a computerized storage device, transformed into a data evaluation set and analyzed. The acquired data can comprise pressure and time information from a first array of pressure sensors disposed in a left shoe and a second array of pressure sensors disposed in a right shoe wherein each pressure sensor in the first array having a corresponding and similarly located pressure sensor in the second array that together form a pressure sensor pair. The data evaluation set can be created by parsing at least some of the acquired data into at least two separate gait phases for each array, calculating a mean pressure value for each sensor for each similar gait phase, and calculating a mean pressure value for each sensor pair for each similar gait phase. The data can be analyzed by comparing, for each gait phase, the mean pressure value for each sensor to the sensor pair mean pressure value and to a mean pressure deviation limit value, and categorizing each sensor into one of at least two pressure uniformity categories for each gait phase on the basis of the comparison. Instead of, or in addition to, using mean data, median data may also be used. The method can also comprise creating a graphical output based on the category into which each sensor has been placed wherein the output shows at least one entire gait cycle wherein each gait phase is individually represented by a right footprint and/or a left footprint. Additionally, the graphical output can show shaded, patterned or colored areas correlating to the pressure uniformity category for each pressure sensor on each footprint for each gait phase in the gait cycle wherein the shaded, patterned or colored areas are shown on each footprint at a location corresponding to the actual sensor location within the shoe. Examples of patterns include, among many others, hatching and repeated use of pre-defined symbols or shapes.

In one exemplary system, a first array of pressure and/or shear stress sensors is configured to be positioned in a left shoe and a first data transmitter is configured to transmit stress, pressure and time data from the first array of pressure and/or shear stress sensors to a data collection device. A second array of pressure and/or shear stress sensors is also configured to be positioned in a right shoe and a second data transmitter is configured to transmit stress, pressure and time data from the second array of pressure and/or shear stress sensors to a data collection device. A data collection device can also be part of the system to receive data from the first and second transmitters.

The system can also include a computer processor constructed and configured to: compare, for at least two separate gait phases, at least a portion of the acquired data to a baseline condition; and to categorize the pressure sensors in each array, or a group of pressure sensors in each array, into one of at least two pressure uniformity categories for each gait phase based on the comparison of the acquired data to the baseline condition. The computer processor can also be constructed and configured to: calculate a mean and/or median pressure value for each sensor for each similar gait phase; calculate a mean and/or median pressure value for each sensor pair for each similar gait phase; compare, for each gait phase, the mean and/or median pressure value for each sensor to the sensor pair mean pressure value and to a mean and/or median pressure deviation limit value; and categorize each sensor into one of at least two pressure uniformity categories for each gait phase on the basis of the comparison of the sensor to the sensor pair.

The disclosed gait analysis system is specifically at least able to record the following parameters while the individual is ambulatory and is engaged in activities of daily living either indoors or outdoors while at home, work and recreational environments: pressures and shear stresses recorded at each individual sensor recorded over time; pressure configurations that may be analyzed as pressure magnitude maps and/or as best-approximation polygons of three or more sides; pressure distribution by area during components of gait cycles; pressure configuration patterns and timing from or between components of gait cycles, including heel strike, mid-stance and toe-off either for a single lower extremity or for comparisons between both lower extremities; total weight-bearing magnitude forces during components of a gait cycle; and the relationship of the above parameters over time within a given gait cycle, e.g., heel strike, mid-stance and toe-off. The analysis of the above mentioned parameters can allow a health care professional to determine if the center of pressure, the shear stress and the resulting torque at the sole is consistent with, as an example, symmetrical weight bearing at the knee joint of the same lower extremity. The data from the soles of both lower extremities can also be analyzed together to determine and to compare the centers of pressure to evaluate if, as an example, symmetrical weight bearing is occurring at the knees and at the hips of both lower extremities and to determine the center of pressure and the pattern of weight bearing is distributed symmetrically to the spine.

BRIEF DESCRIPTION OF THE DRAWINGS

FIG. 12 is an example input table for the gait analysis system of FIG. 1

FIG. 13 is a first example output table from the gait analysis system of FIG. 1.

FIGS. 14-16 show a second example output table from the gait analysis system. of FIG. 1

DETAILED DESCRIPTION

Figure 1:
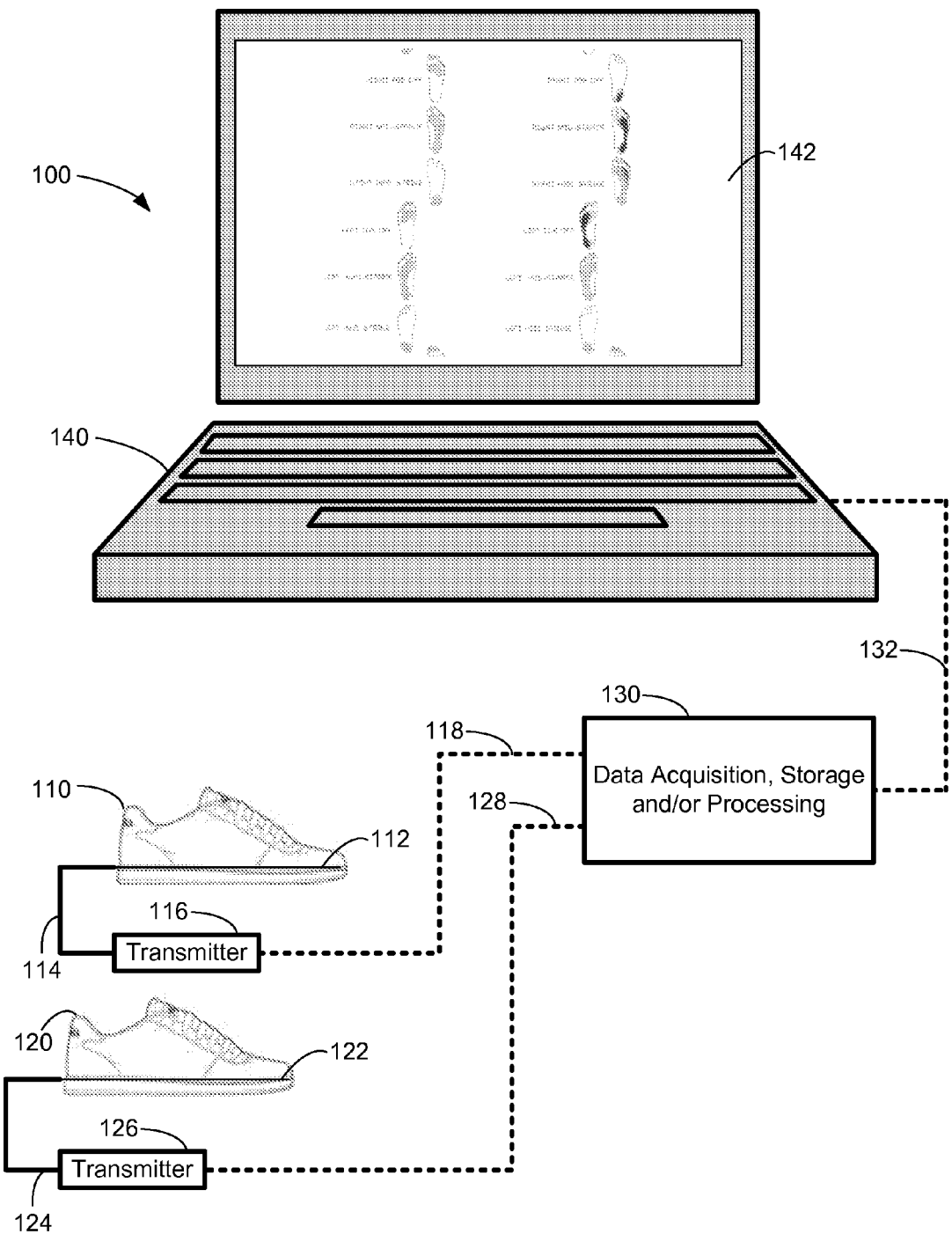
FIG. 1 is a schematic view of a first embodiment of a gait analysis system.

This disclosure relates to a system and methods for analyzing the gait of an individual. In broad terms, pressure data from a left shoe and a right shoe are acquired and evaluated to determine if an individual's gait is in need of improvement. One example of such a system is gait analysis system 100, shown on FIG. 1.

In one exemplary embodiment, gait analysis system 100 includes a first array of sensors 112 disposed within a right shoe 110 and a second array of sensors 122 disposed within a left shoe 120. Many types of sensors are useful in gait analysis system 100. For example, sensors 112a,122a can be pressure sensors. Alternatively, the sensors can be shear stress sensors 152a, 162a, for example biaxial shear stress sensors. By the use of the term "biaxial" it is meant that at least two component values for shear stress are measured along different axes, preferably orthogonal axes. In some arrangements, both biaxial shear stress sensors and pressure sensors will be used in the same shoe.

Figure 2A:
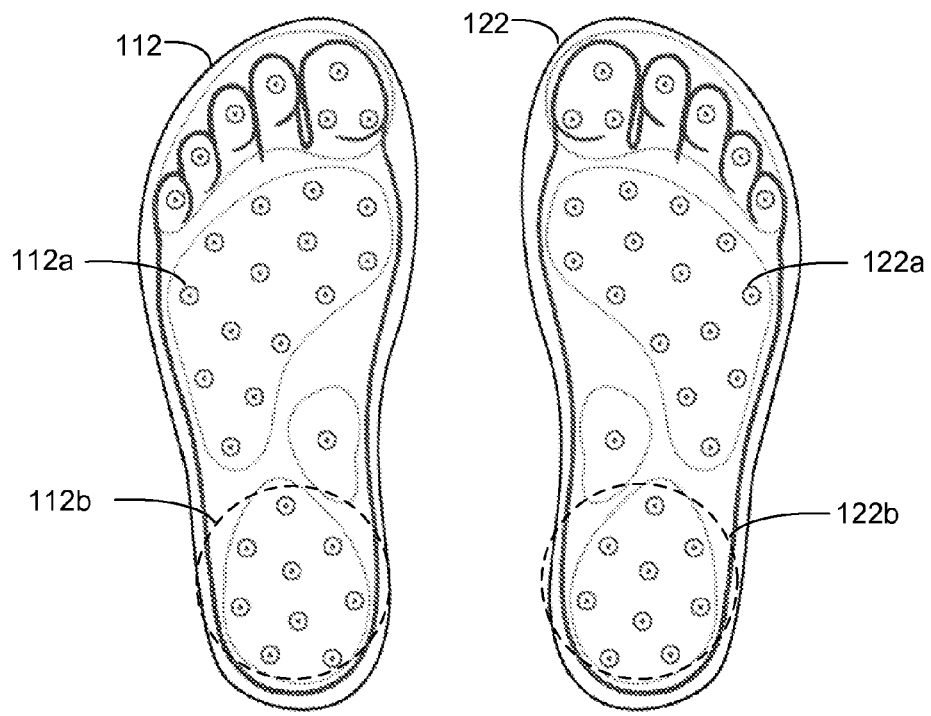
FIG. 2a is a diagrammatic top view of an arrangement of pressure sensors for a left shoe and a right shoe.
Figure 2B:
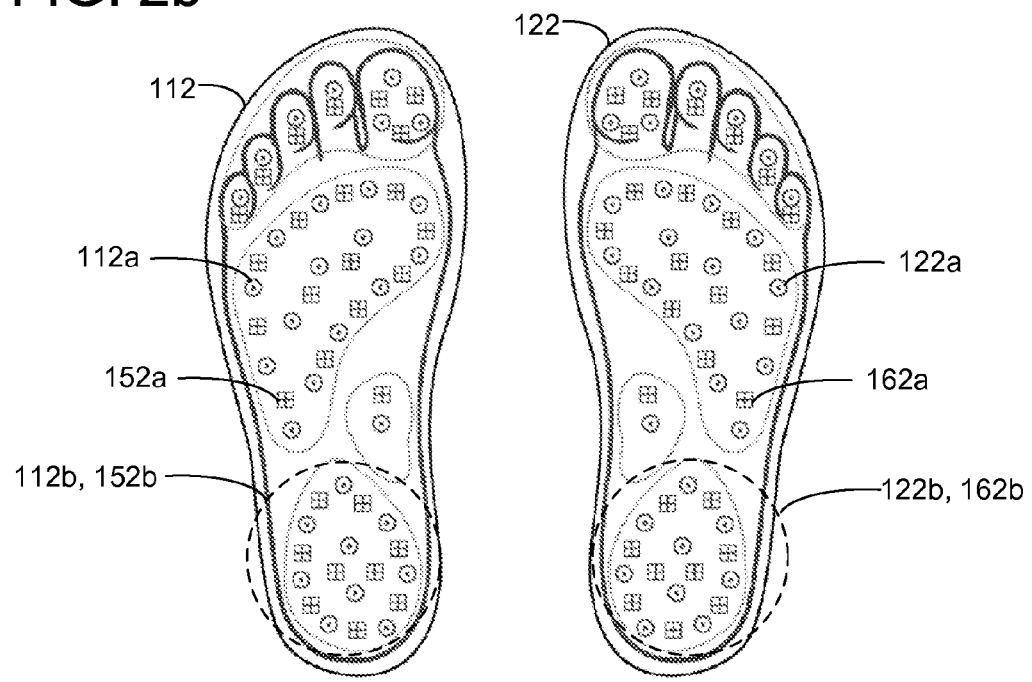
FIG. 2b is a diagrammatic top view of an arrangement of pressure sensors and shear stress sensors for a left shoe and a right shoe.

In the particular embodiment shown in FIG. 2a, the first and second arrays of sensors 112, 122 are for measuring the pressure that an individual's foot exerts over an area of the foot. In the embodiment shown in FIG. 2b, the first and second arrays of sensors 112, 122 are for measuring not only the pressure, but also the shear stress that an individual's foot exerts over an area of the foot. Many types and configurations of pressure sensors and shear stress sensors, and combinations thereof are suitable for this purpose. For example, FIG. 2a shows a plurality of pressure sensors 112a,122a disposed in various locations to form a first and second array of pressure sensors 112, 122, respectively. FIG. 2b shows a plurality of pressure sensors 112a, 122a and a plurality of shear stress sensors 152a,162a disposed in various locations to form a first and second array of pressure sensors 112, 122, respectively. As can be seen at FIGS. 2a and 2b, each array includes numerous individual sensors arranged to cover the major contacting areas of a foot (only type of sensor in each array is actually labeled). Of course, the arrays 112, 122 could be configured with fewer or more sensors, or in conjunction with a pressure sensing fabric.

In the actual arrangement shown in FIGS. 2a and 2b, each sensor 112a,152a in the first array 112 has a correspondingly located sensor 122a,162a in the second array 122 to form a sensor pair. As shown at FIGS. 2a and 2b, the two pressure sensors actually labeled 112a and 122a form such a pair as do sensors 152a and 162a. Also, some of the sensors can be grouped together such that an output is generated based on the average output for the grouped sensors. In this case, rather than having sensor pairs, the sensors that are grouped together would form group sensor pairs 112b,122b and/or 152b,162b. Where a fabric is used, the same principle can be applied to pre-defined areas over the fabric. Additionally, it should be noted that the first and second pressure arrays 112, 122 can be integral to a shoe, or can be arranged on a removable insert. In the latter case, a potential benefit exists in that the pressure arrays 112, 122 can be used in conjunction with an individual's normally used shoes.

Gait analysis system 100 can also include transmitters 116, 126 for receiving and transmitting output information from the first and second pressure arrays 112, 122 to unit 130, discussed later. As shown in FIG. 1, the transmitters 116, 126 are connected to the first and second arrays 112, 122 via connections 114, 124, respectively. Connections 114, 124 can be made via either cable(s) or a wireless connection. As shown, connections 114, 124 are cables that are directly connected to each sensor 112a,122a while connections 118 and 128 to unit 130 are wireless connections. However, one skilled in the art will appreciate that other configurations are suitable. For example, some of the sensors can be wired together or selectively grouped via software such that an output is generated based on the average pressure output for grouped sensors, 122b.

As noted in the preceding paragraph, gait analysis system 100 can also include a unit 130 for receiving data from the transmitters 116, 126. As shown, unit 130 is configured to acquire sensor output information, such as time, stress and pressure values, from the first and second arrays 112, 122 via transmitters 116, 126. Unit 130 can also be configured to store the data from the transmitters and to perform calculations relating to the data. In either case, unit 130 can also be configured to upload and download information from a computer 140 via connection 132. As shown, connection 132 is a wireless connection, but a cable connection is just as feasible. Additionally, computer 140 can also be configured with a display screen 142 to show graphical output generated either by unit 130 or computer 140. Non-limiting examples of information that could be uploaded to the computer 140 from unit 130 are raw pressure data from the pressure sensors (e.g. output voltage and time), raw data from the shear stress sensors, calculated results such as mean and/or median values for the pressure data over a period of time, net torque exerted across a group of shear stress sensors, and graphical output information. Non-limiting examples of information that could be downloaded to unit 130 from computer 140 are configuration parameters, such as specific times to acquire output data, desired sensor groupings, and parameters for defining individual gait phases. It should also be noted that many of the above described functions for transmitters 116, 126, unit 130 and computer 140 do not necessarily need to be performed by one device or the other. For example, the calculations necessary to create a graphical representation could be performed by the computer 140 instead of unit 130.

Figure 3:
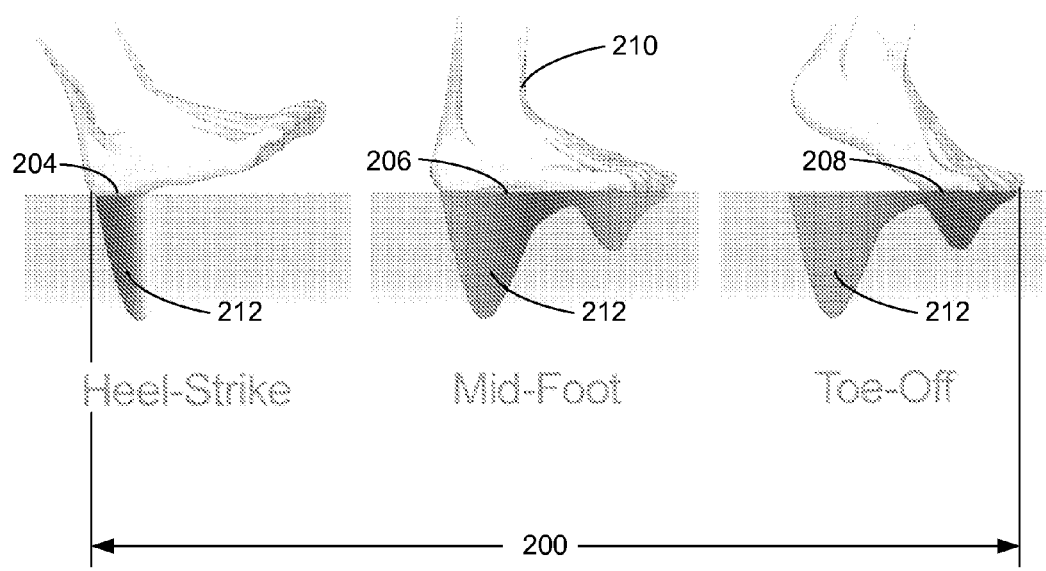
FIG. 3 is a representation of three gait phases for a right foot during a single gait cycle.

Referring to FIGS. 4-8, exemplary graphical outputs are shown that can be displayed on an electronic display, such as screen 142, and/or generated in hard copy form. In each of FIGS. 4-8, a gait pattern with footprints is shown representing an intended direction of ambulation 214 wherein each individual footprint represents a separate gait phase 202. The shown gait phases shown for each foot are heel strike 204, mid-stance 206, and toe-off 208. Each gait phase 202 corresponds to a segment of time during which the foot or shoe is in contact with the ground such that the sum of all three gait phases represents the total contact time. To further illustrate this concept, these three gait phases are also shown in FIG. 3 which depicts a side view of an individual's right foot 210 and representative pressure values 212 as the foot moves through each gait phase 204, 206, 208. Taken together, the gait phases for each foot form one entire gait cycle 200. A gait cycle 200 is defined as all defined gait phases for sequentially adjacent left and right foot placements. In the particular embodiments shown in FIGS. 4-8, gait cycle 200 is comprised of the following gait phases 202 from the bottom of the page up: left heel strike 204, left mid-stance 206, left toe-off 208, right heel strike 204, right mid-stance 206, and right toe-off 208. It is, of course, possible to parse the contact time into fewer or more than the three gait phases shown for each foot. It is also possible to show only the gait phases for a gait cycle 200 of only one foot where an analysis is not concerned with both feet. In such a case the system would only require the collection of data from sensors associated with the foot to be analyzed.

Still referring to FIGS. 4-8, shaded areas are shown for each footprint and gait phase to represent pressure values. With specific reference to FIG. 5, arrows are also shown to represent shear stress and torque values. These shaded areas and arrows are for showing whether an individual's gait is in conformity with a baseline condition. Many examples exist for a baseline condition. In one example, the baseline condition can be a model of calculated values for pressure, shear stress, and/or torque over time that represents a typical gait, or a gait having no apparent abnormalities. In such an example, the model can be based upon an individual of the same or similar physical characteristics, including height, weight, gender, as the individual being analyzed. In this case, the shaded areas would represent the difference between the actual gait of the individual and the modeled gait. Another example is where the baseline condition is derived from values obtained from a previous gait/balance test or from an initial gait baseline test for the individual being analyzed. In this case, the shaded areas would represent any changes that have occurred since the baseline test or the previous test. Yet another example is where the baseline condition is actually the combined sensor data from the sensor pair associated with each sensor. Where this is the case, the shaded areas represent the degree to which one foot is exerting more or less pressure, shear stress or torque than the mean value for both feet at a particular location for each gait phase. Any of these baseline conditions is equally useful when looking at sensor data on an individual output basis, or when looking at aggregated sensor data that has been averaged together to create a mean value for each gait phase. When looking at individual output values, the comparison is useful to assess a specific event, such as the conditions that led up to an individual's loss of balance and subsequent fall. When looking at mean and/or median values for each gait phase, the comparison is useful to longitudinally assess an individual's typical gait throughout the course of a day, which may vary significantly from a simple baseline test in a laboratory setting. It is noted that the graphical output can be configured to selectively show one or more of the shaded areas, the shear stress arrows, and the torque arrows such that only the representations relevant to the analysis are shown.

In the exemplary embodiments shown in FIGS. 4-8, the shaded areas are shown in three gray-scale tones: dark gray, medium gray, and light gray. These tones can represent different pressure uniformity categories relating to the comparison of the pressure sensor data to the baseline condition. For example, dark gray represents a "non-uniform high" category wherein the pressure sensor data are above the baseline condition, medium gray represents a "uniform" category wherein the pressure sensor data are within the baseline condition, and light gray represents a "non-uniform low" category wherein the pressure sensor data are below the baseline condition. The "uniform category" can correlate to a baseline condition that is defined by a range of acceptable values. This could be accomplished by selecting a high value and a low value that bound the baseline condition. Alternatively, the range could be defined by a mean value and a mean deviation limit wherein the range extends from the mean value minus the mean deviation limit to the mean value plus the mean deviation limit. In a similar fashion, median values can also be used. In either case, the non-uniform high and non-uniform low categories would correlate to values above or below the baseline condition, respectively. With such an approach, a health care professional can simply vary the mean deviation limit for a particular individual in order to account for the fact that some gait/balance disorders require a more sensitive assessment than others. Additionally, although FIGS. 4-8 are shown using a three-tone grayscale representation that relate to three pressure uniformity categories, one skilled in the art will appreciate that more tones/colors and categories may be used to show a higher degree of resolution.

It is noted that the shaded areas shown are derived from data collected from the pressure sensors and subsequent calculations. Although the sensors are located in discreet positions within the shoe, the graphical output can be created such that a smooth, gradated pressure pattern is achieved, as shown in FIGS. 4-8. However, it is entirely possible to show segmented regions on the graphical output such that the output for each pressure sensor is more clearly identified. Showing an entire gait cycle 200 with shaded areas in the manner described is beneficial because many gait and balance disorders can be more easily evaluated with such visual information.

Figure 4:
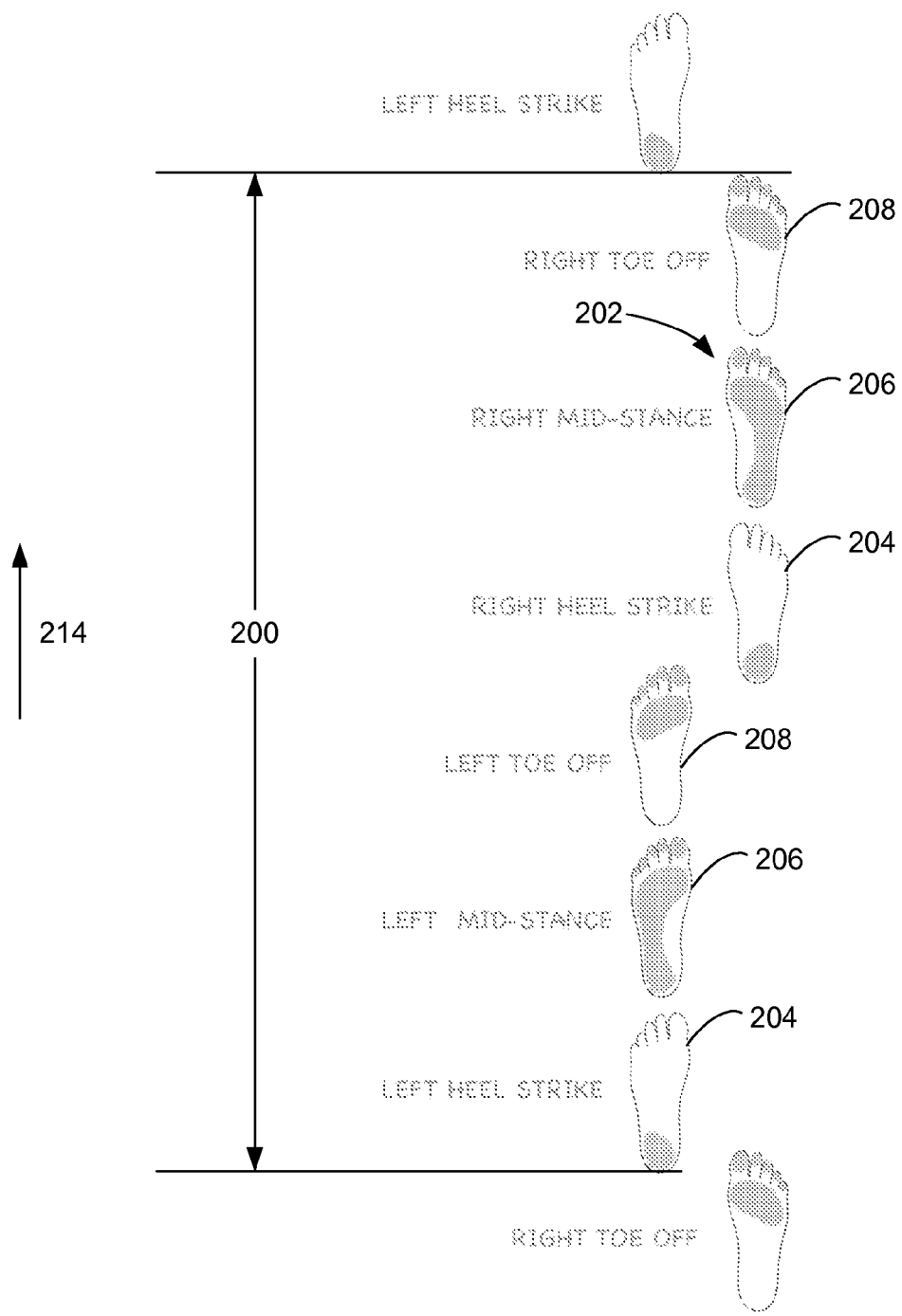
FIG. 4 is a first example of a graphical output from the gait analysis system of FIG. 1.
Figure 5:
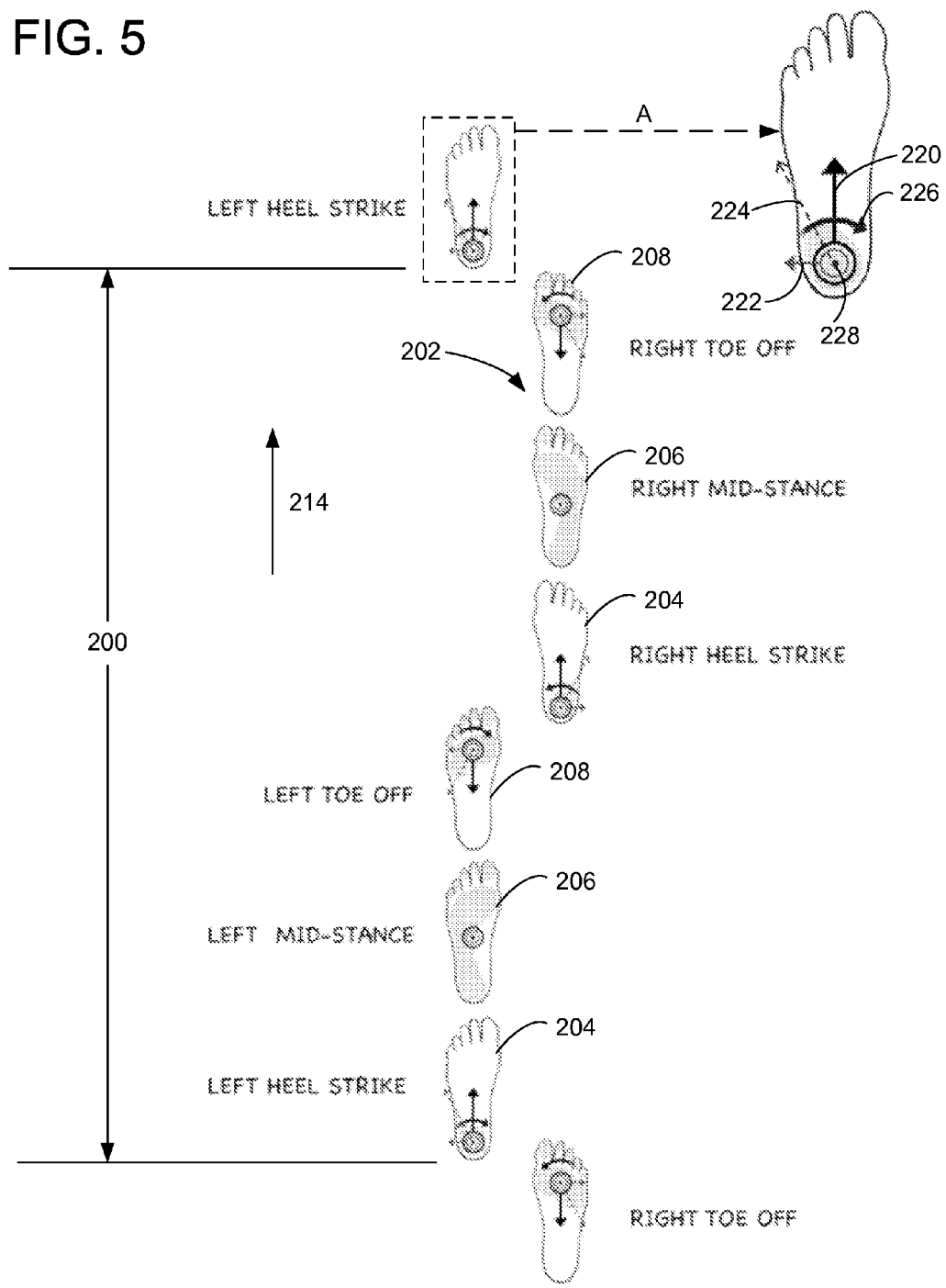
FIG. 5 is a second example of a graphical output from the gait analysis system of FIG. 1.

With particular reference to FIGS. 4-5, the shaded areas for the gait cycle shown represent output derived from a comparison of the pressure sensor values against a baseline condition where all of the pressure sensor values are within the baseline condition parameters for each gait phase. This can be readily seen by the condition that all of the shaded areas in FIG. 4 are medium gray. Such output is the result of an individual's gait that is either normal, consistent with a previous test and/or in a balanced state, depending upon the nature of the baseline condition utilized.

Figure 6:
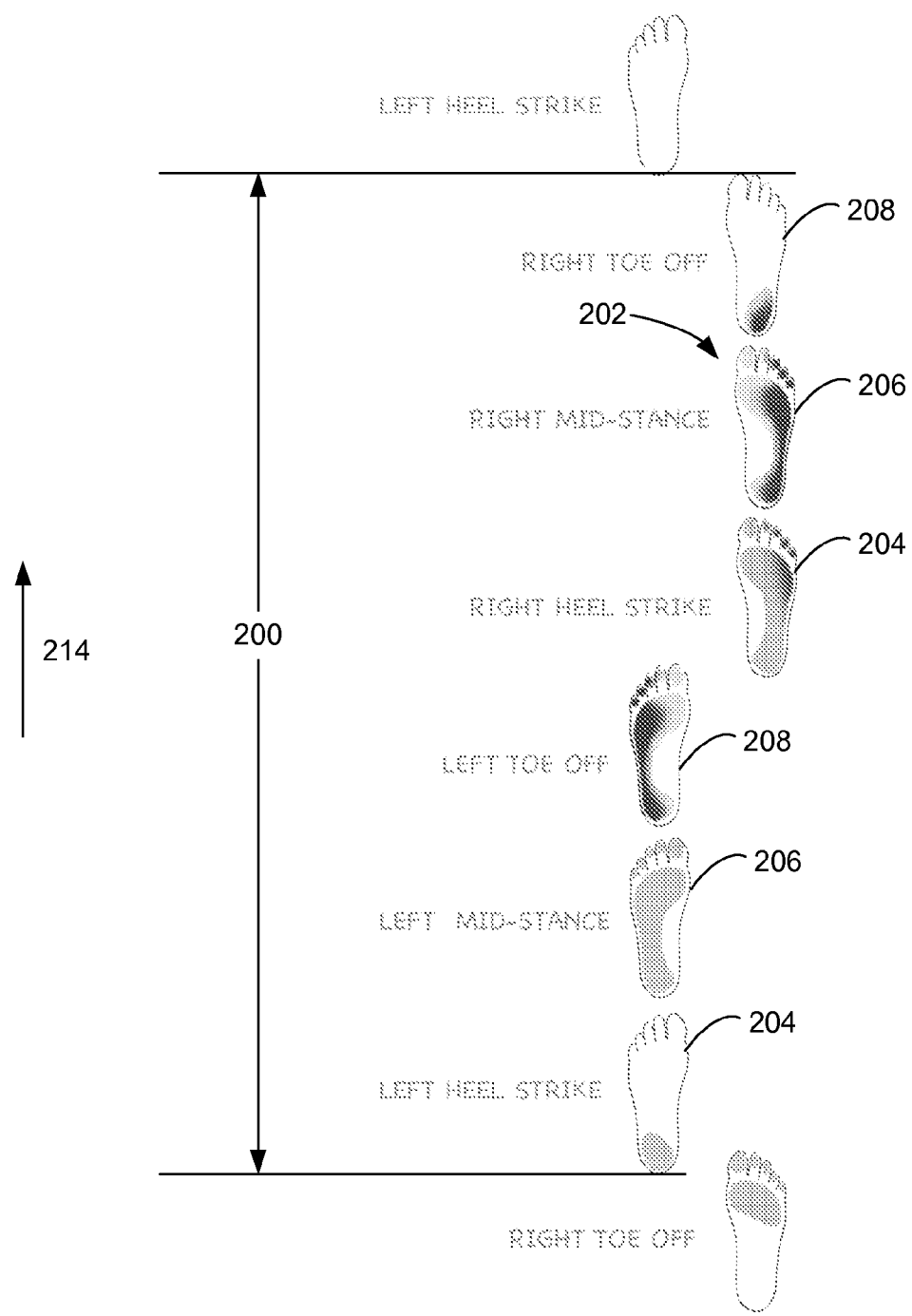
FIG. 6 is a third example of a graphical output from the gait analysis system of FIG. 1.

Output from an individual with a balance disorder that can lead to a fall is shown in FIG. 6. As shown in FIG. 6, the shaded areas indicate that the individual is going from heel strike to mid-stance and then back to heel strike. During this gait cycle, the individual stays in mid-stance and alternates pressure on the lateral aspect of the sole and then to the medial aspect of the sole and then back again. By viewing the entire gait cycle in this manner, a health care professional is better able to evaluate and understand the circumstances leading up to and surrounding a loss of balance event that may have led to a fall. The baseline condition for the output shown in FIG. 6 is a set of pressure values corresponding to a normal gait pattern.

Figure 7:
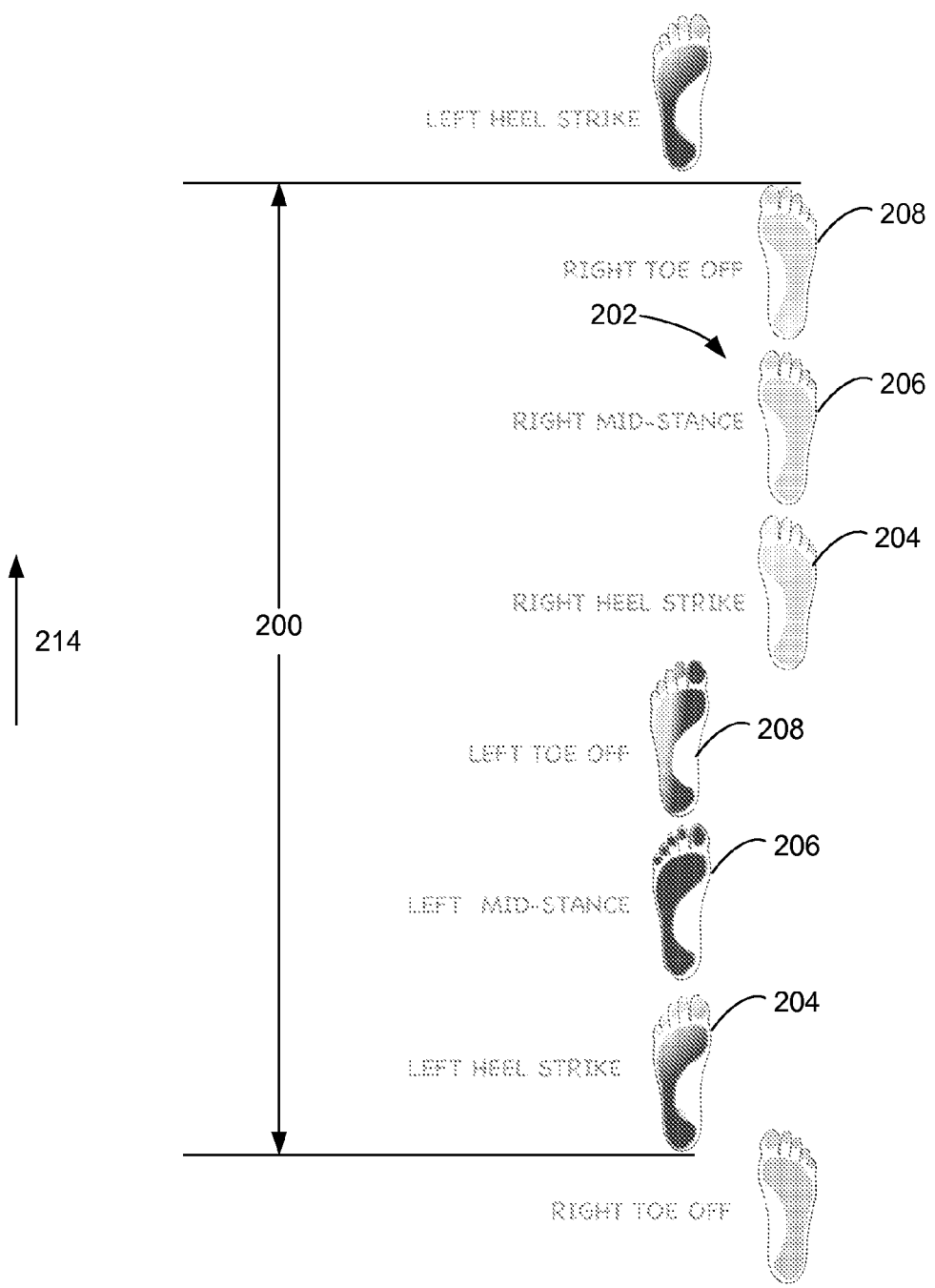
FIG. 7 is a fourth example of a graphical output from the gait analysis system of FIG. 1.

Another example of a useful graphical output is shown at FIG. 7 where longitudinal pressure sensor data over a period of time has been collected and averaged to create mean values for each gait phase. Here, an individual with pain or other dysfunction at any point in either or both lower extremities may adopt a gain that imbalances weight-bearing and thereby transmits imbalanced musculoskeletal, mechanical forces to the spine. These imbalanced forces may be associated with back pain. The use of the gait analysis system and the associate graphical output will help to assess the balance or lack thereof by allowing a quantitative, comparative analysis of the pressure patterns and proportions of pressure being exerted on the two different lower extremities over time. The baseline comparison for the output shown in FIG. 7 is a set of pressure values corresponding to a normal gait pattern.

Figure 8:
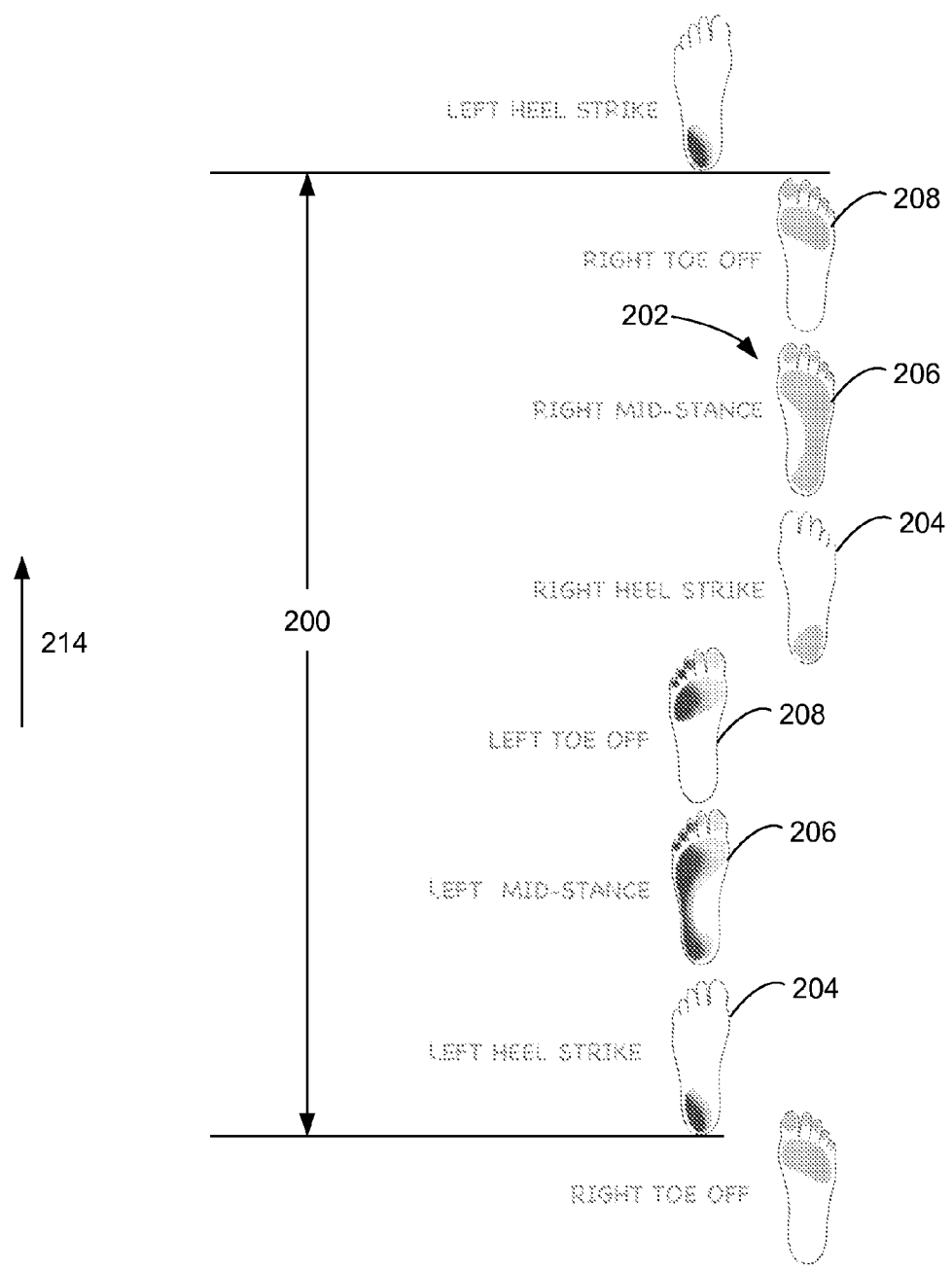
FIG. 8 is a fifth example of a graphical output from the gait analysis system of FIG. 1.
Figure 9:
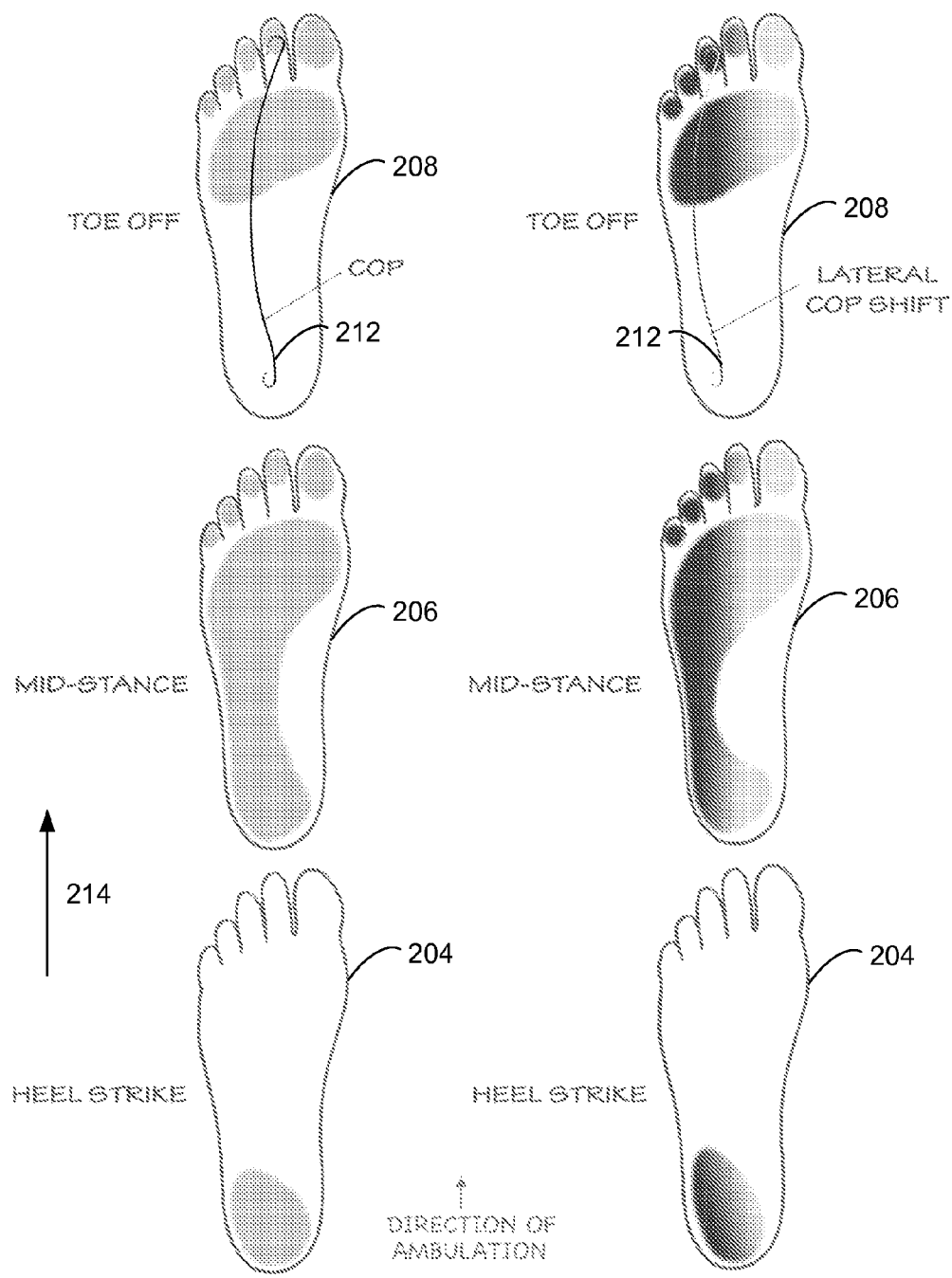
FIG. 9 is a further representation of the fourth example shown in FIG. 7.

Yet another example of how showing at least a single gait cycle is beneficial is represented in FIG. 8 where longitudinal pressure sensor data over a period of time has been collected and averaged to create mean values for each gait phase. Here, an individual with osteoarthritis of the knee associated with pain in the lateral aspect of that knee may adopt an abnormal and deleterious gait. Such a gait might relieve pain in the short term and accelerate knee joint destruction more quickly over time. The physiologic basis is to partially unload the painful lateral aspect of that same knee by modifying components of the gait cycle to focus weight-bearing on the lateral aspects of the sole of the foot of that extremity. By so doing, most of the weight-bearing is shifted to the medial aspect of that knee joint. Such a change in gait can be detected by measurement and analysis of the graphical output showing at least a single gait cycle. In order to prevent further or more rapid deterioration of that knee joint, gait training, including strength training, may be instituted and then monitored by the gait analyses system over time. This condition is also partially represented at FIG. 9 where it is further shown how the center of pressure (COP) of the foot undergoes a lateral shift. The graphical output for any of the depictions shown in FIGS. 4-8 can also show the COP of the foot, or a variance between the actual COP and a baseline condition COP. The baseline comparison for the output shown in FIG. 8 is a set of pressure values corresponding to a normal gait pattern.

Referring back to FIG. 5, additional graphical information is presented regarding an individual's gait that is not shown in FIG. 4. Specifically, FIG. 5 shows shear stress direction and magnitude arrows for each gait phase in addition to applied torque for each gait phase. Such information is enabled by locating biaxial shear stress sensors within the shoes 110, 120. In the particular embodiment shown, the total shear stress 224 is broken down into a longitudinal shear stress 220 component and a lateral shear stress component 222. For the purpose of clarity, these features are labeled on an enlarged footprint indicated by dashed arrow A. The length, color and/or width of each of the shown arrows 220, 222, 224 can be related to the raw magnitude of the stress experienced by the sensor. Alternatively, and as described previously for the pressure values, the length and/or width of each arrow 220, 222, 224 can reflect the result of a comparison of measured values to a baseline condition. For example, the measured shear stress values from a baseline test can be compared to those acquired during a subsequent test. In this case, the magnitude of the shear stress arrows would reflect the difference between the baseline and subsequent test. Additionally, the direction of the shear stress arrows 220, 222, 224 can be oriented to show the actual direction of the shear stress applied along the measured axis, or the net direction of shear stress when compared to a baseline condition. It is noted that the direction and relative magnitude of the arrows in FIG. 5 are schematic and not intended to represent an actual or expected output from the system. In the example shown in FIG. 5, the longitudinal shear stress arrow 220 changes from a force applied in a direction extending from the heal towards the toes during the heal strike gait phase 204, to a net zero force during the mid-stance gait phase, to a force applied in a direction extending from the toes towards the heal during the toe off gait phase. Through the use of the shear stress sensors, it is also possible to calculate a torque value for each gait phase, and to show a torque value arrow 226. Similarly to the shear stress arrows, the direction and length/width/color of the torque arrow 226 can change depending on the magnitude and direction of the torque applied to the shoe. Furthermore, the torque arrow 226, and the shear stress arrows 220, 222, 224 can be arranged about a central axis 228 that corresponds to the center of the applied torque. It is also noted that other methods for graphically depicting the magnitude and direction of the shear stress and torque values besides the use of arrows is possible without departing from the concepts presented herein. Furthermore, one skilled in the art will appreciate that values for these parameters can be presented in tabular form wherein pressure, stress and torque can be shown in isolation or together for easier viewing and analysis.

Figure 10:
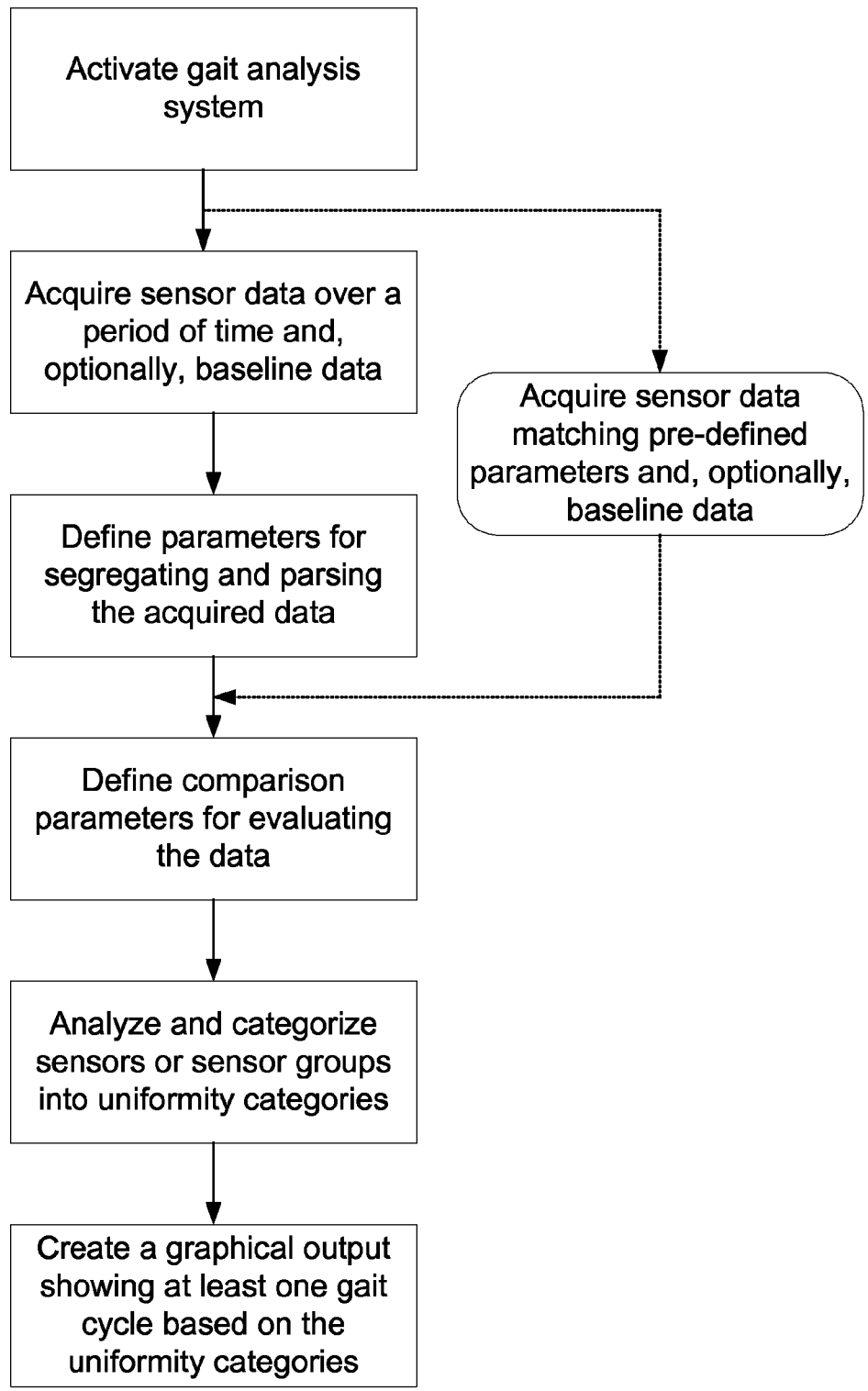
FIG. 10 is a flow chart showing example steps for analyzing an individual's gait.

Referring to FIG. 10, a flow chart is shown that demonstrates steps that can be used to arrive at the above described graphical output examples by using the gait analysis system 100. In a first step, the gait analysis system 100 is activated. This step can include outfitting the individual with the shoes 110, 120 and unit 130, and enabling unit 130 to start recording data. After the gait analysis system 100 is activated, unit 130 can acquire sensor and time data over either a predetermined or open ended period of time. If desired, the health care professional can guide the individual through a series of tests which can be used to establish an initial baseline. This initial baseline can be used as the baseline condition, or can be compared to another baseline condition for further analysis. The initial baseline can include activities such as walking, running, and walking up or down stairs. During the actual testing period, unit 130 will collect data until it is deactivated. After a desired period of time has passed, or a desired amount of data has been collected, unit 130 can be returned to the health care professional for analysis of the data.

Another step is for the health care professional to define parameters for segregating and parsing the acquired data. Alternatively, the parameters can be pre-configured in the system such that no input is needed from the health care professional. This step can be performed before or after the previously described step of acquiring the sensor data. If this step is performed before the data acquisition step, unit 130 can also be configured to acquire only sensor data that is within the specified parameters rather than simply collecting all data. Alternatively, a desired data subset can be extracted from the acquired data set after data acquisition is complete. One example of a parameter for segregating the data includes specifying that only data recorded during ambulatory periods is collected and/or analyzed. This can be accomplished in unit 130 by monitoring for gait cycles that occur, for example within a predefined period of time. This can also be accomplished through interaction with a user interface, such as a button, that the individual can use to identify periods of ambulation. An example of a parameter for parsing the acquired data to be analyzed includes defining how sensor data are grouped into individual gait phases. This can be accomplished by defining gait phases as a percentage of the contact time. For example, the gait phases can be defined as: 1) heel strike phase being 0% to 15% of the total foot contact time with the ground; 2) mid-stance phase being between 15% and 55% of the contact time; and 3) toe off phase being 55% to 100% of the contact time. One skilled in the art will recognize that other methods for parsing the acquired data to be analyzed into separate gait phases are also possible. Another parameter for parsing the acquired data can be the specification of how pressure sensor readings are grouped together.

Another step in the shown process is to define comparison parameters for evaluating the acquired data. The comparison parameters are for setting up an analysis that will allow a uniformity category to be assigned to each pressure sensor, or sensor group, in the arrays. An example of a parameter for a comparison parameter is the definition of the baseline condition. As stated previously, the baseline condition can be established through a mean value and a mean deviation or variation threshold limit, or through the selection of a range of values. Alternatively, the baseline condition can be defined by a mean value, an upper deviation limit and a lower deviation limit. Furthermore, the baseline condition can be established through the use of values derived from a baseline test, a previous analysis, or a calculated normal gait for the individual. In the above examples, the baseline condition enables the use of three possible outputs in that the acquired data will either be above, below or within the baseline condition. It is also noted that multiple baseline conditions can be established through the use of multiple deviation limits, multiple ranges, or by other methods known in the art. As stated previously, the relationship of the sensor values to the baseline condition provides the basis for categorizing the sensor or senor groups into uniformity categories.

Figure 11:
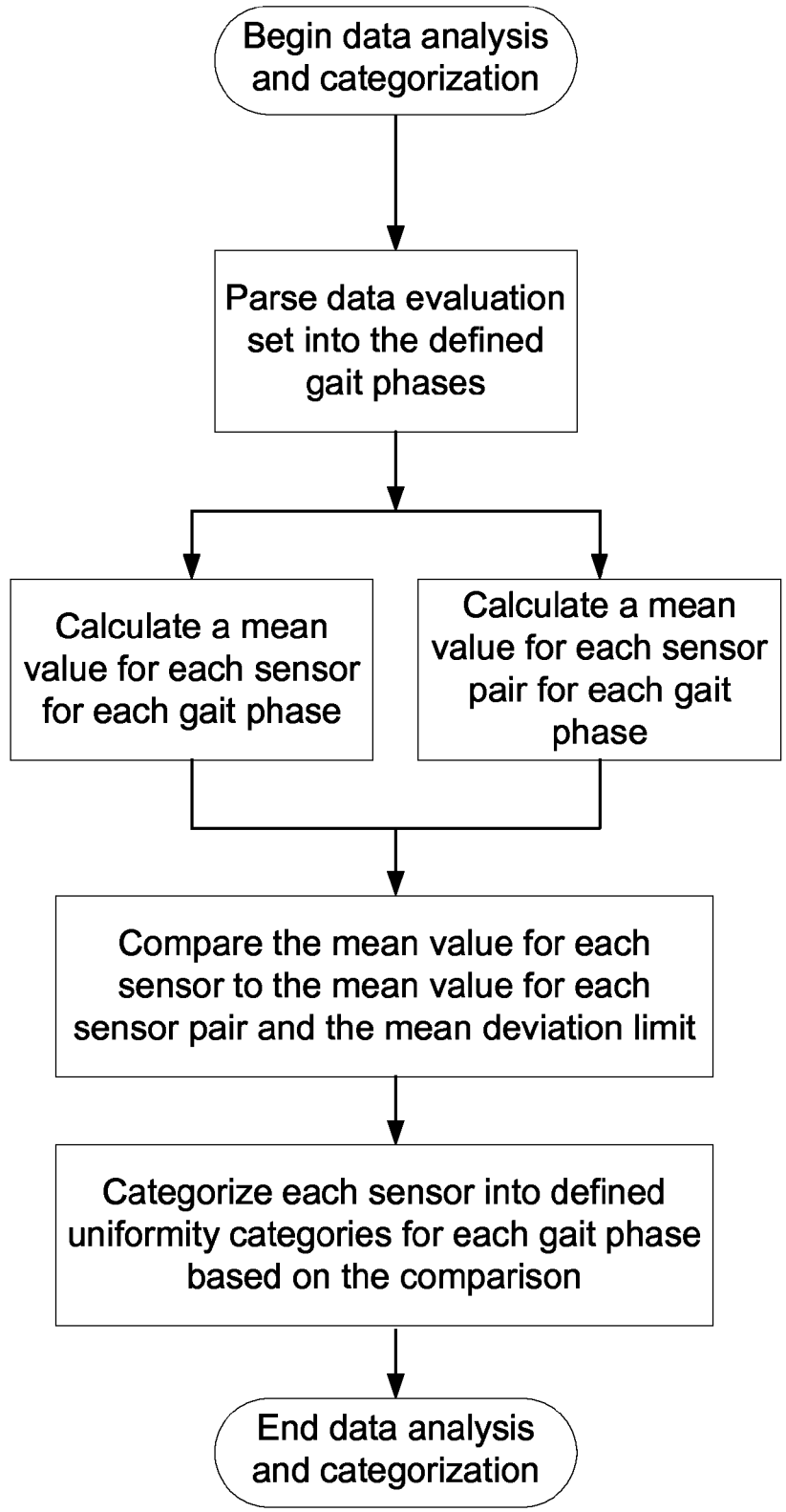
FIG. 11 is a flow chart showing example steps for analyzing and categorizing acquired data.

After all of the parameters or all of the selected parameters of interest have been established, it is then possible for the gait analysis system to perform the necessary calculations on the acquired data in order to assign an appropriate uniformity category. One example of how these calculations can be performed is shown in FIG. 11 where gait analysis system 100 acquires data over a period of time which is then parsed into separate gait phases based on the defined parameters. After this step, a mean value is calculated for each sensor for all readings acquired during each gait phase. In this example, a mean value is also calculated for each sensor pair for all readings acquired during each gait phase. The sensor pair mean value and a mean deviation limit value will thus serve as the baseline condition against which the individual pressure sensor mean values are compared. As such, a subsequent calculation step will be to determine whether each individual sensor mean value is within, above or below the baseline condition. Once this calculation is complete, the system can then categorize each sensor into a uniformity category that is correlated to the relationship between the sensor mean value and the baseline condition. As stated before, median values can be used in addition to, or instead of, mean values.

Referring back to FIG. 10, once the categorization of the sensors and/or sensor groups has occurred, the system can then create a graphical output showing at least one complete gait cycle based on the uniformity categories. This is essentially accomplished by assigning a color or tone to each pressure uniformity category. However, it should be noted that it is possible to arrive at the graphical output shown in FIGS. 4-8 without explicitly defining a uniformity category by simply assigning a color or tone to a mathematical comparison of the sensor data to the baseline condition directly. In either case, the graphical output is the direct result of a comparison between the sensor data and the chosen baseline condition. As such, a uniformity category will exist whether or not actually defined in the system explicitly. It is further contemplated that a health care professional can change any of the above identified parameters to generate additional graphical outputs without the need to acquire additional data. For example, the health care professional may want to compare the sensor data to a baseline condition relating to a normal gait, and also to a previous test for the same individual to monitor progress over time towards an ideal gait pattern. Another example would be where the health care professional wants to narrow or broaden the values for the baseline condition to evaluate more or less extreme patterns in the individual's gait. Furthermore, the gait analysis system 100 is also capable of displaying input and output tables, such as those shown in FIGS. 12-16, which can provide a link to the graphical output for a particular gait cycle, or for an exemplary gait cycle. FIG. 12 shows sample input data while FIG. 13 shows output data values for a baseline data test. An output table showing a comparison between a subsequent test and the baseline test is shown at FIGS. 14-16. It is also possible for the graphical output system to allow the health care professional to scroll the graphical output to see all of the gait cycles that have been recorded which is particularly useful in analyzing the events that may have led up to a loss of balance and fall. As such, one skilled in the art will appreciate that gait analysis system 100, and the graphical output it is able to provide, greatly enhances a health care professional's ability to diagnose and treat balance and gait disorders.

Given the above description it should be appreciated that gait analysis system 100 is able to provide quantitative data during activities of daily living that can be used to identify individuals who may be at risk for gait and/or balance disorders, and the potentially injurious consequences of those disorders. Gait analysis system 100 is also able to enhance a health care professional's ability to aid and monitor the rehabilitation and training of individuals who either have or are at risk for gait and/or balance disorders.

The above are example principles. Many embodiments can be made.

We claim:

1. A method for analyzing the gait of an individual wearing a left shoe and a right shoe, the method including the steps of:
    (a) acquiring data onto a computerized storage device:
        (i) the acquired data comprising pressure and time information being from a first array of pressure sensors disposed in a left shoe and a second array of pressure sensors disposed in a right shoe;
        (ii) each pressure sensor in the first array having a corresponding and similarly located pressure sensor in the second array that together form a pressure sensor pair;

(b) creating a data evaluation set, including the steps of:
  (i) parsing at least some of the acquired data into at least two separate gait phases for each array;
  (ii) calculating a mean pressure value for each sensor for each similar gait phase; and
  (iii) calculating a mean pressure value for each sensor pair for each similar gait phase;
(c) analyzing the data evaluation set, including the steps of:
  (i) comparing, for each gait phase, the mean pressure value for each sensor to the sensor pair mean pressure value and to a mean pressure deviation limit value; and
  (ii) categorizing each sensor into one of at least two pressure uniformity categories for each gait phase on the basis of the comparison; and
(d) creating a graphical output based on the category into which each sensor has been placed, the output showing at least one entire gait cycle wherein each gait phase is individually represented by a right footprint and a left footprint.

2. The method according to claim 1, wherein:
(a) the graphical output shows shaded, patterned or colored areas correlating to the pressure uniformity category for each pressure sensor on each footprint for each gait phase in the gait cycle, the shaded, patterned or colored areas also being shown on each footprint at a location corresponding to the actual sensor location within the shoe.

3. The method according to claim 2, wherein each shaded, patterned or colored area is blended or transitioned together with an adjacent shaded, patterned or colored areas.

4. The method according to claim 1, wherein the step of parsing at least some of the acquired data into at least two gait phases includes parsing the data into a heel strike gait phase, a mid-stance gait phase, and a toe-off gait phase.

5. The method according to claim 1, wherein the mean pressure deviation limit value is the same for all gait phases.

6. The method according to claim 1, wherein the mean pressure deviation limit value is different for all gait phases.

7. The method according to claim 1, wherein one of the pressure uniformity categories is defined by sensor pressure values that equal to or exceed the sum of the mean pressure value for the sensor pair and the mean pressure deviation limit.

8. The method according to claim 1, wherein one of the pressure uniformity categories is defined by sensor pressure values that equal to or are less than the mean pressure value for the sensor pair minus the mean pressure deviation limit.

9. The method according to claim 1, wherein one of the pressure uniformity categories is defined by sensor pressure values that are equal to or between:
(a) the mean pressure value for the sensor pair minus the mean pressure deviation limit; and
(b) the sum of the mean pressure value for the sensor pair and the mean pressure deviation limit.

10. The method according to claim 1, wherein only data is acquired that meets predefined criteria.

11. The method according to claim 10, wherein the predefined criteria includes data relating to ambulatory periods of the individual using the shoes.

12. The method according to claim 1, wherein the step creating a data evaluation set further includes selecting portions of the acquired data to analyze.

13. The method according to claim 12, wherein the selected portions of the acquired data to analyze includes data relating to ambulatory periods of the individual using the shoes.

14. The method according to claim 1, wherein the mean deviation pressure limit value is a function of the mean pressure value for each sensor pair.

15. The method according to claim 14, wherein the mean deviation pressure limit value is defined as being plus or minus 25% of the mean pressure value of the sensor pair such that values over 25% of the mean are categorized into one uniformity category, values under minus 25% of the mean are categorized into a different uniformity category, and all other values are categorized into a third category.

16. The method according to claim 1, wherein the steps of acquiring data, creating a data evaluation set, and analyzing the data evaluation set are performed on a single computerized device.

17. The method according to claim 1, wherein the data are acquired through a wireless data connection.

18. A system for analyzing the gait of an individual wearing a left shoe and a right shoe, the system comprising:
(a) a first array of pressure sensors configured to be positioned in a left shoe and a first data transmitter configured to transmit pressure and time data from the first array of pressure sensors to a data collection device;
(b) a second array of pressure sensors configured to be positioned in a right shoe and a second data transmitter configured to transmit pressure and time data from the second array of pressure sensors to a data collection device, wherein each pressure sensor in the first array has a corresponding and similarly located pressure sensor in the second array that together form a pressure sensor pair;
(c) a data collection device configured to receive data from the first and second transmitters and to acquire the data onto a computerized storage device wherein the acquired data comprises pressure and time information from the first array of pressure sensors and the second array of pressure sensors; and
(d) a computer processor constructed and configured to;
  (i) parse at least some of the received data into at least two separate gait phases for each array;
  (ii) calculate a mean pressure value for each sensor for each similar gait phase; and
  (iii) calculate a mean pressure value for each sensor pair for each similar gait phase;
  (iv) compare, for each gait phase, the mean pressure value for each sensor to the sensor pair mean pressure value and to a mean pressure deviation limit value; and
  (v) categorize each sensor into one of at least two pressure uniformity categories for each gait phase on the basis of the comparison;
(e) wherein an electronic display is configured to display an output based on the category into which each sensor has been placed, the output showing at least one entire gait cycle wherein each gait phase is individually represented by a right footprint and a left footprint.

19. The system of claim 18, wherein the data collection device and the computer process are housed within the same unit.

* * * * *